United States Patent [19]
Schwemberger et al.

[11] Patent Number: 5,609,604
[45] Date of Patent: Mar. 11, 1997

[54] TROCAR WITH IMPROVED BLADE ATTACHMENT

[75] Inventors: Richard F. Schwemberger; Darrel Powell, both of Cincinnati; Randy R. Stephens, Fairfield; Salvatore Privitera, West Chester, all of Ohio

[73] Assignee: Ethicon Endo-Surgery, Inc., Cincinnati, Ohio

[21] Appl. No.: 543,547

[22] Filed: Oct. 16, 1995

[51] Int. Cl.$^6$ ........................................... A61B 17/34
[52] U.S. Cl. ........................ 606/185; 604/164; 604/264
[58] Field of Search ..................... 604/164, 264; 606/185, 167; 30/340, 342, 366, 60, 162, 71

[56]  References Cited

U.S. PATENT DOCUMENTS

| | | | |
|---|---|---|---|
| 1,333,745 | 3/1920 | Wescott | 604/272 |
| 3,643,649 | 2/1972 | Amato | 606/185 |
| 3,831,814 | 8/1974 | Butler | 604/274 |
| 4,535,773 | 8/1985 | Yoon | 604/51 |
| 4,601,710 | 1/1986 | Moll | 604/274 |
| 5,314,417 | 5/1994 | Stephens et al. | 604/264 |
| 5,344,410 | 9/1994 | Kolkin et al. | 604/264 |
| 5,441,041 | 8/1995 | Sauer et al. | 606/185 |

FOREIGN PATENT DOCUMENTS

| | | | |
|---|---|---|---|
| 0647434A2 | 4/1995 | European Pat. Off. | A61B 17/34 |
| 160504 | 8/1903 | Germany | 30/340 |

*Primary Examiner*—Michael Powell Buiz
*Assistant Examiner*—Patrick W. Rasche
*Attorney, Agent, or Firm*—Matthew S. Goodwin

[57] ABSTRACT

A trocar having an obturator with an obturator housing, a piercing tip and a rigid stem is disclosed. The piercing tip has a cutting edge surface and first and second spaced-apart legs generally parallel to each other extending away from the cutting edge surface. The stem is attached to the obturator housing at a first end of the obturator, and the legs of the piercing tip straddle the stem at an opposite end of the obturator. The straddling of the legs about the stem of the obturator fixes the piercing tip to the stem. The attachment of the piercing tip to the stem provides a secure attachment. The trocar is easy to manufacture and assemble, and the component parts can be readily disassembled. The piercing tip attachment is especially advantageous when the piercing tip is configured generally as a razor blade.

15 Claims, 5 Drawing Sheets

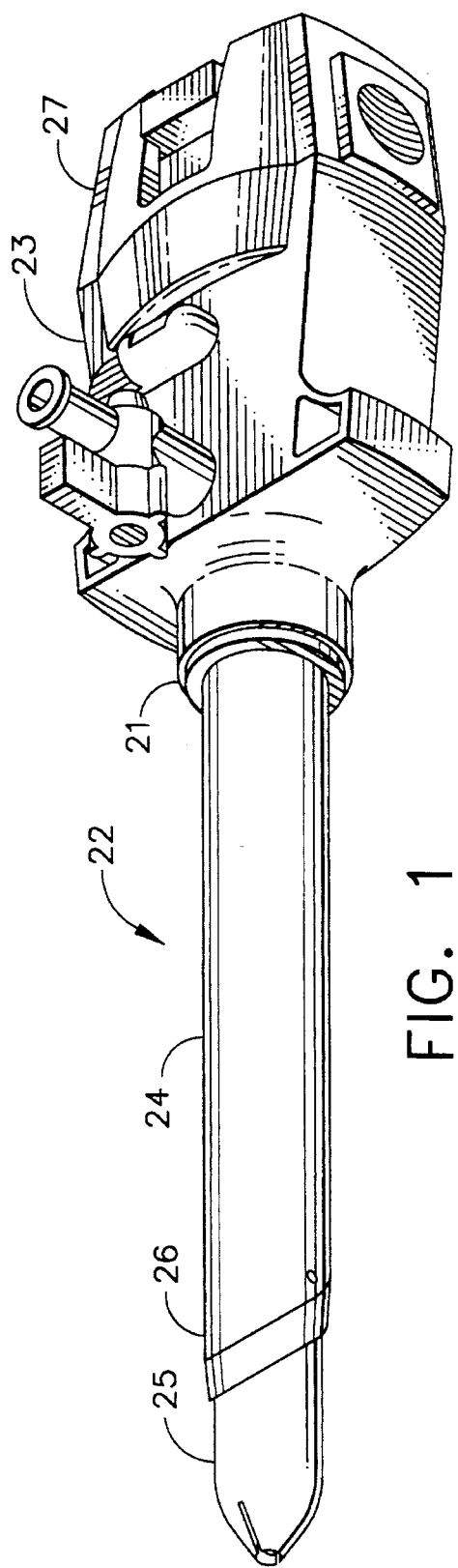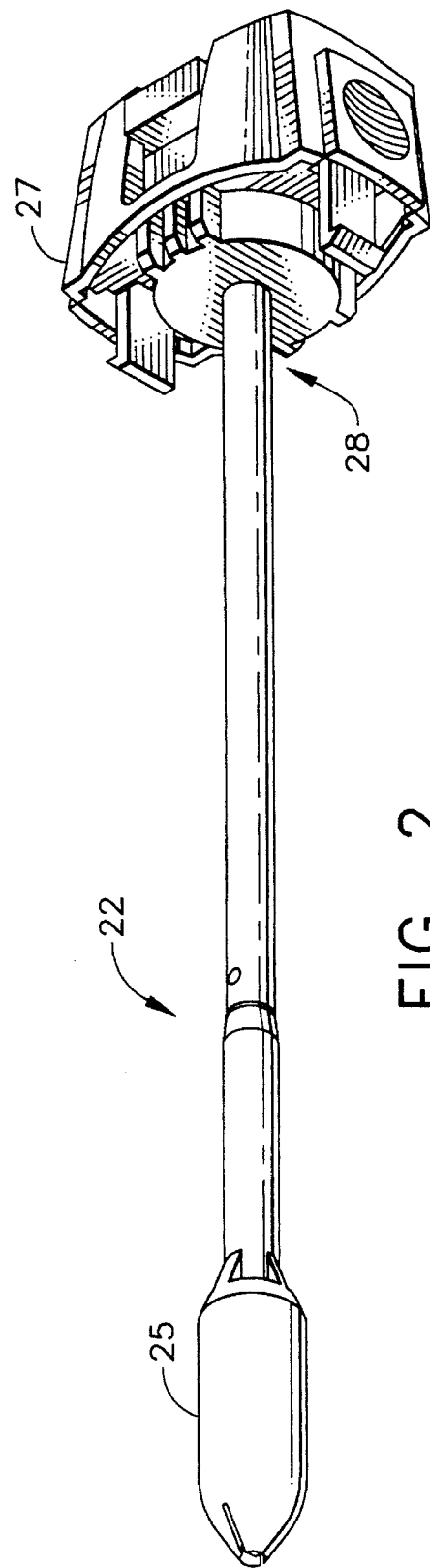

TROCAR WITH IMPROVED BLADE ATTACHMENT

BACKGROUND OF THE INVENTION

This invention relates to a trocar for puncturing the body wall to provide access to a surgical site during endoscopic surgery. More specifically, it relates to a trocar having an obturator which incorporates a puncturing tip, and the unique attachment of the tip to the supporting stem of the obturator.

The surgical trocar has become the mainstay in the development and acceptance of endoscopic surgical procedures. Endoscopic surgery involves the performance of surgery through a number of openings having a relatively small diameter. These openings are made with the trocar, which typically includes a trocar obturator and a trocar cannula. The obturator is the piercing implement which punctures the body wall to make the opening. The obturator slidingly fits into the trocar cannula, which is essentially an access tube. The obturator is initially fitted into and through the cannula so that the piercing tip of the obturator extends from the distal end of the cannula. Pressure is exerted on the body wall with the piercing tip, and the puncture is made through the body wall. Once the puncture is made, the obturator is withdrawn from the cannula. The cannula then provides a small diameter passageway into and through the body wall to provide access for additional surgical instrumentation to the desired surgical site.

One of the significant advances in the development of the trocar is described in U.S. Pat. No. 4,535,773. This patent describes the use of a spring-loaded safety shield interposed between the obturator and inner wall of the trocar cannula. In its unbiased position, the shield covers the puncturing tip of the obturator. When pressure is applied against the body wall, the shield retracts to expose the blade. When the body wall is punctured, the pressure is relieved and the safety shield springs back to cover the puncturing tip. In this way, inadvertent puncture of internal organs is substantially lessened.

The puncturing tip of the trocar obturator has conventionally been configured in the shape of a cone or a pyramid. More recently, it has been found that a flat, razor blade can provide less trauma to tissue during puncture. See, for example, U.S. Pat. No. 5,314,417. Regardless what tip geometry is used, it is necessary during the manufacture of the trocar obturator to attach the puncturing tip to the remaining components of the obturator. In essence, the obturator consists of three primary components. These components are the obturator handle, stem and puncturing tip. The handle is the component which the user grips when puncturing the body wall. At the opposite end of the obturator handle is the puncturing tip. Supporting the puncturing tip and providing the connection between the tip and the obturator handle is the stem. The stem is typically a long, rigid rod. The connection between the stem and the puncturing tip is critical for safe and efficient performance of the trocar. This may be especially true depending on the particular geometrical configuration of the puncturing tip.

The puncturing tip of an obturator conventionally includes a collar or thread for fastening the tip to the stem of the obturator. Alternatively, the tip may simply incorporate a notch, and the stem may be press fit into the notch. Although these attachment techniques may be adequate under normal conditions, they may be inadequate when high loads or rotational torque is present at the puncturing tip as the body wall is being punctured. Additionally, when the puncturing tip is a flat razor blade as described in the '417 patent, the connection between the blade and the stem may not provide the optimum transition from the blade to the stem to reduce trauma to the tissue as the trocar is inserted into the tissue.

Accordingly, an improved trocar is needed within the surgical community. In particular, this trocar would have an obturator which incorporates an improved attachment between the puncturing tip of the obturator and its stem. This attachment ideally would be easy to assemble and provide a puncturing tip which is secure and resists pull-off and torque during high loads. Further, such an ideal attachment would not require additional obturator parts, and would also enable the user to disconnect the stem from the puncturing tip if desired. Finally, when a safety-shielded trocar with a flat, razor blade obturator tip is used, the connection between the tip and the stem of the obturator would provide a smoother transition from the tip to the stem, and ultimately to the safety shield, so that trauma to tissue as the tissue is punctured is substantially reduced.

SUMMARY OF THE INVENTION

The invention is a surgical trocar which comprises an obturator. The obturator has an obturator housing at a first end of the obturator, a piercing tip at an opposite end of the obturator for piercing bodily tissue, and an elongated, rigid stem.

The piercing tip of the obturator includes a cutting edge surface and first and second spaced-apart legs generally parallel to each other. The legs extend away from the cutting edge surface of the piercing tip.

The stem of the obturator connects the obturator housing to the piercing tip of the obturator. The stem is attached to the obturator housing at a first end of the obturator. At the opposite end of the obturator, the legs of the piercing tip straddle the stem. The straddled legs fix the piercing tip of the obturator to the stem.

The straddling of the legs of the piercing tip about the stem provides a secure attachment of the piercing tip to the stem of the obturator, and resists detachment under heavy load conditions when the trocar is penetrating bodily tissue. In addition, the straddled legs provide high torque resistance, and therefore the penetrating tip resists detachment from the stem when the trocar is twisted or rotated during use.

The trocar of this invention is easy to manufacture and assemble. It has three basic components: a) an obturator housing, b) an elongated stem, and c) a piercing tip. Additional components or sophisticated assembly techniques are unnecessary. Correspondingly, the components of the trocar are easily disassembled, particularly the piercing tip from the stem, if desired.

In a particularly preferred embodiment, the piercing tip has first and second planar surfaces generally parallel to each other, and these surfaces converge to the cutting edge surface of the piercing tip. In other words, the piercing tip is configured similar to a razor blade. When the piercing tip is configured as a razor blade, in certain embodiments the straddling of the legs of the blade about the stem of the obturator can facilitate a smooth transition from the blade surfaces to the stem. Accordingly, the bodily tissue may be steadily dilated as the trocar is penetrated through the tissue progressively from the cutting edge surface to the obturator stem. When the bodily tissue dilates, puncturing or tearing of the tissue is reduced or prevented, therefore reducing the size of the incissional wound resulting from the penetration of the trocar through the body wall.

The trocar of this invention can be used in all of the surgical procedures where conventional trocars have been used or contemplated. Of course, the trocar of this invention is particularly adapted to provide access to a surgical site during endoscopic surgery.

BRIEF DESCRIPTION OF THE DRAWINGS

FIG. 1 is a perspective view of a preferred surgical trocar of this invention.

FIG. 2 is a perspective view of the obturator assembly for the surgical trocar illustrated in FIG. 1.

DETAILED DESCRIPTION OF THE PREFERRED EMBODIMENT

Figure 3:
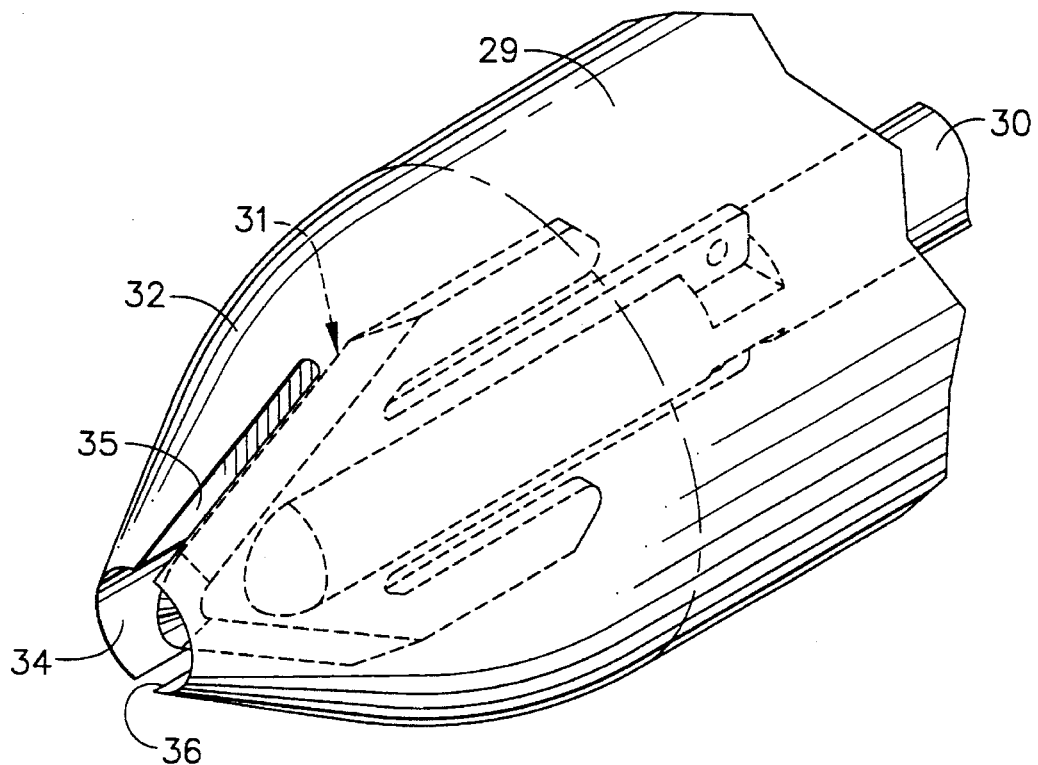
FIG. 3 is a perspective view of the distal end of the preferred trocar illustrating the safety shield of the trocar in its extended position to cover the piercing tip of the obturator.

A preferred surgical trocar 20 is depicted generally in FIGS. 1 and 2. The trocar has a cannula 21 and an obturator assembly 22. The cannula includes a cannula housing 23 and a tube 24 extending from the housing. The obturator assembly slides through the cannula, and it can be inserted into or withdrawn from the cannula. The distal end 25 of the obturator assembly protrudes from the distal end 26 of the cannula tube when the obturator assembly is inserted fully through the cannula. When it is inserted fully, the obturator housing 27, which is attached at the proximal end 28 of the obturator assembly, is mated with the proximal end of the cannula housing.

Figure 4:
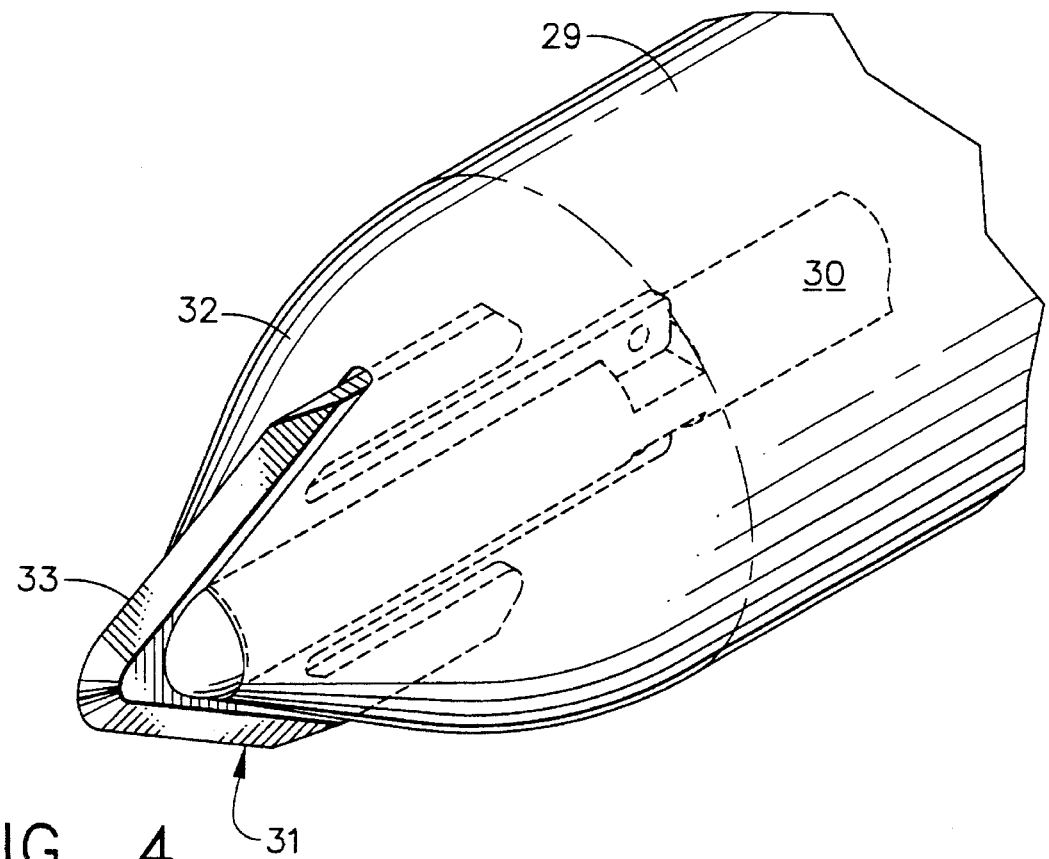
FIG. 4 is a perspective view similar to that of FIG. 3, except that the safety shield is in its retracted position to expose the cutting edge surface of the piercing tip of the obturator.
Figure 5:
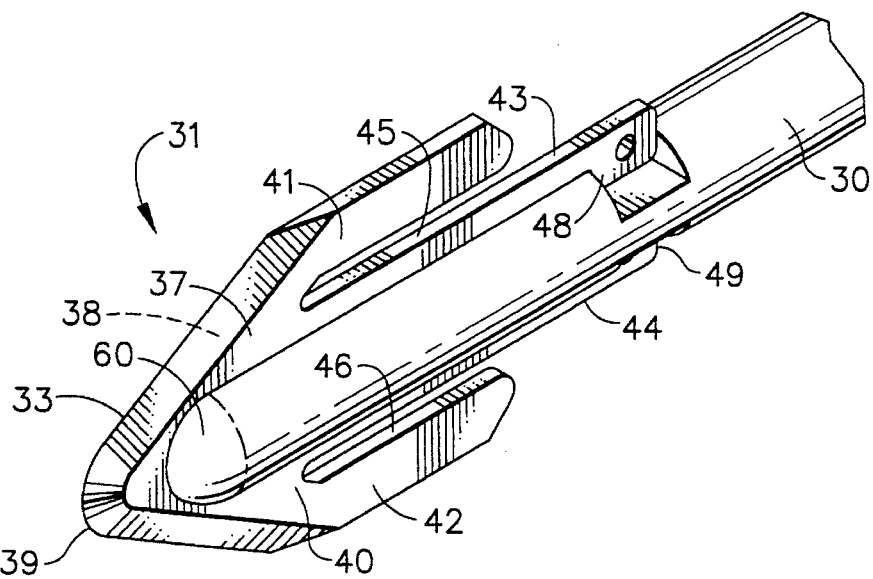
FIGS. 5–7 are perspective views illustrating the attachment of the piercing tip of the obturator illustrated in FIGS. 3 and 4 to the obturator stem in a preferred embodiment of this invention.
Figure 6:
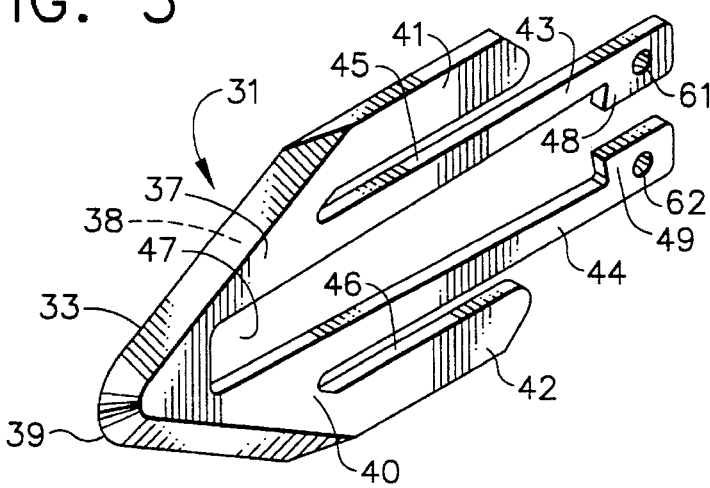
Figure 7:
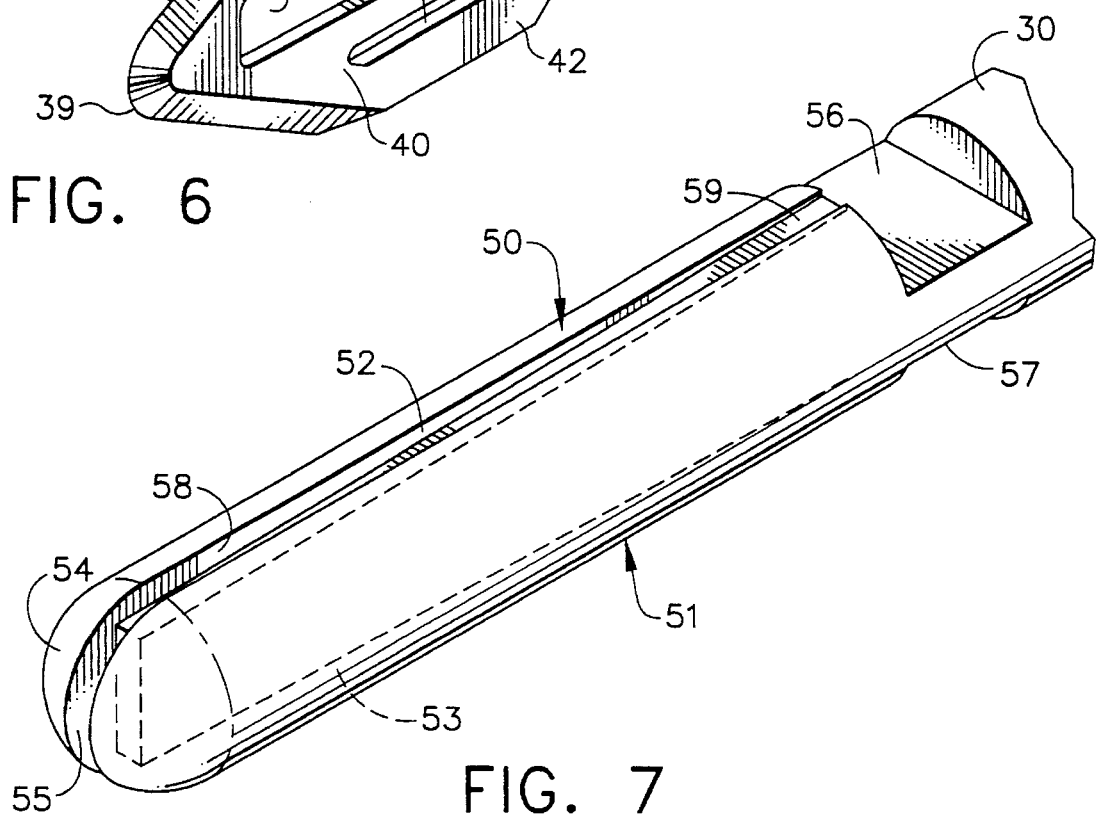
Figure 8:
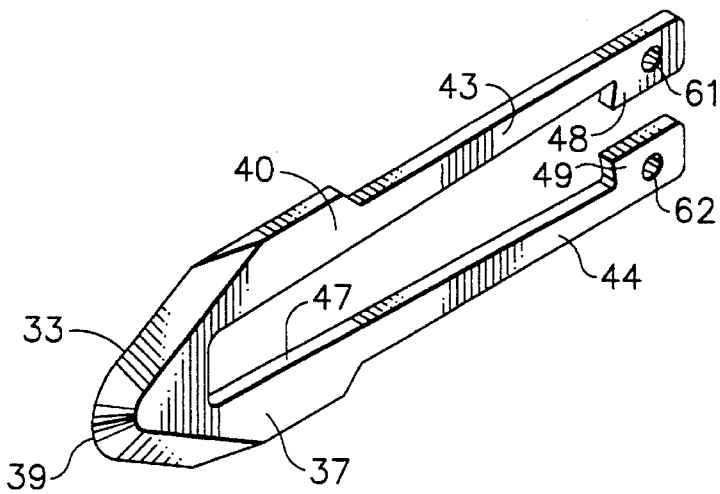
FIG. 8 is a perspective view of an alternate embodiment for the piercing tip of the obturator.
Figure 9:
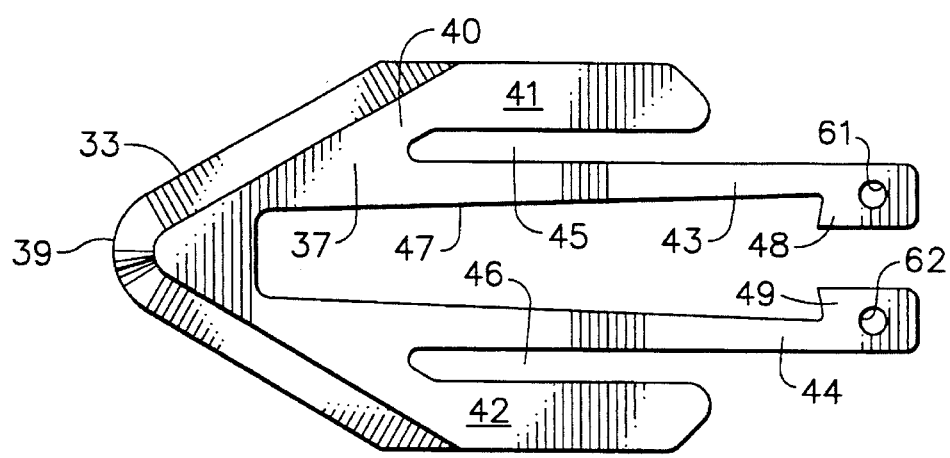
FIGS. 9 and 10 are plan and side elevation views, respectively, of the piercing tip of the obturator illustrated in FIGS. 3–6.
Figure 10:
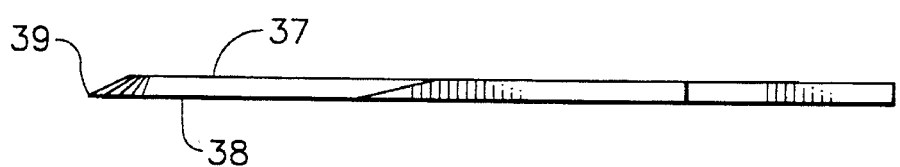
Figure 11:
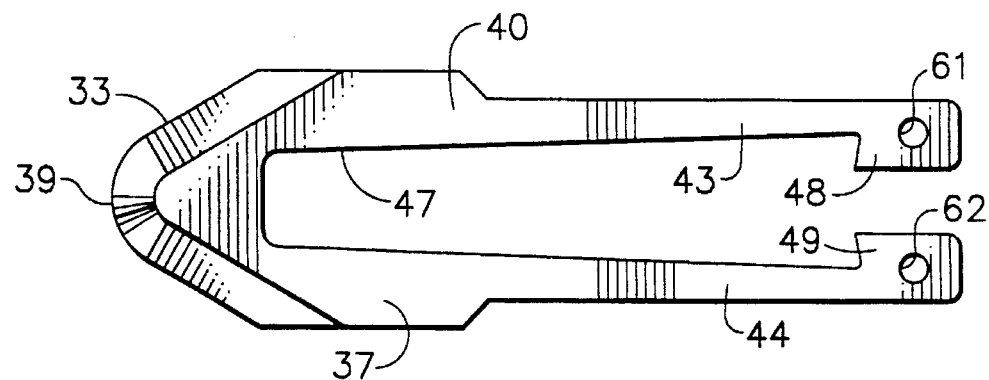
FIGS. 11 and 12 are plan and side elevation views, respectively, of the alternative piercing tip illustrated in FIG. 8.
Figure 12:
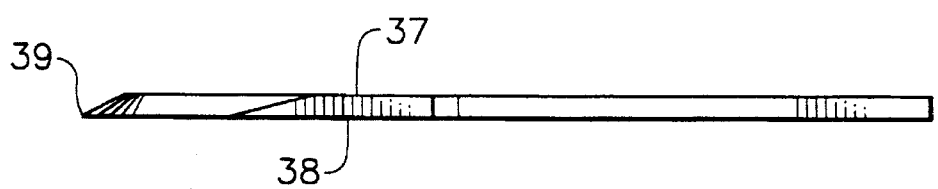

Referring now to FIGS. 3 and 4, the obturator assembly includes an obturator 9 which has a long, rigid stem 30. The stem connects the obturator housing of the obturator with a piercing tip 31. The piercing tip is attached to the stem at the distal end of the stem. The obturator assembly also includes a safety shield 32 which encases the piercing tip. When the safety shield is in its extended position, as illustrated in FIG. 3, the distal end of the safety shield covers the piercing tip. When the shield is retracted, as depicted in FIG. 4, the cutting edge surface 33 of the piercing tip is exposed. The cutting edge surface protrudes through a central opening 34 and first and second vertical slits, 35 and 36, respectively, displayed at the distal end of the safety shield.

The particular features of the preferred piercing tip and the obturator stem to facilitate attachment of the tip to the stem are illustrated in FIGS. 5–7, 9 and 10. The piercing tip has first and second planar surfaces, 37 and 38, respectively, which are generally parallel to each other. The surfaces converge to form the cutting edge surface 33 of the piercing tip. The cutting edge surface is triangular, and has a rounded apex 39. Extending from the base 40 of the triangular cutting edge surface are first and second elongated base portions, 41 and 42, respectively. Additionally, first and second legs, 43 and 44, respectively, extend in a direction away from the cutting edge surface of the piercing tip. The legs are spaced apart from each other, and generally parallel to each other. The legs are located interior of the elongated base portions. First and second longitudinal slots, 45 and 46, respectively, separate the elongated base portions from the legs. The distance between the legs defines an interior slot 47 within the piercing tip. The interior slot is displayed through the planar surfaces of the tip adjacent the cutting edge surface. At the end of the first and second legs, there are mutually opposed, inwardly extending barbs, 48 and 49, respectively.

The distal end of the obturator stem 30 to which the piercing tip is attached has first and second sidewalls, 50 and 51, respectively. Embedded within the sidewalls at about 180° from each other are first and second tapered slots, 52 and 53, respectively. At the distal tip 54 of the obturator stem, a tip slot 55 is interposed between the first and second slots so that a continuous attachment slot for the piercing tip is formed. Rearward of the distal tip of the obturator stem, and at the terminus of the first and second slots, there are first and second notches, 56 and 57, respectively. The length of the slots and the location of the notches are coincident with the length of the legs and barbs on the piercing tip. The first and second slots are tapered from a deep region 58 adjacent the tip slot to a shallow region 59 adjacent the notches.

The piercing tip is attached to the obturator stem by sliding the legs of the piercing tip rearwardly from the distal tip of the obturator stem toward the notches within the first and second tapered slots. The legs act as cantilevered springs as they slide within the tapered slots. Consequently, the legs snap into the notches when the barbs on the legs slide off the shallow region of the tapered slots. When the barbs snap into the notches, the piercing tip is securely embedded within the attachment slot. In this way, a secure attachment resistant to high loads and rotational torque is provided.

A particularly noteworthy feature of the piercing tip attachment illustrated in FIGS. 5–7, 9 and 10 is the transition created between the cutting edge surface and the obturator stem to facilitate less traumatic piercing of bodily tissue. The distal tip 60 of the obturator stem is rounded. The rounded tip is adjacent the cutting edge surface because the interior slot 47 defining the spaced-apart legs of the piercing tip extends adjacent the cutting edge surface. Consequently, when the piercing tip is attached to the obturator stem, the rounded distal tip of the stem is positioned adjacent the cutting edge surface. Therefore, as tissue is pierced with the cutting edge surface, it will gradually dilate when it contacts the rounded tip of the obturator stem. Accordingly, a smooth transition between the flat cutting edge surface and the elongated stem of the obturator is provided.

Another noteworthy feature of the attachment in FIGS. 5–7, 9 and 10 is the ease with which the piercing tip can be attached to and disassembled from the obturator stem. First and second extraction holes, 61 and 62, respectively, are displayed on the first and second barbs of the legs of the piercing tip to facilitate the removal of the piercing tip from the stem, if desired.

Figure 13:
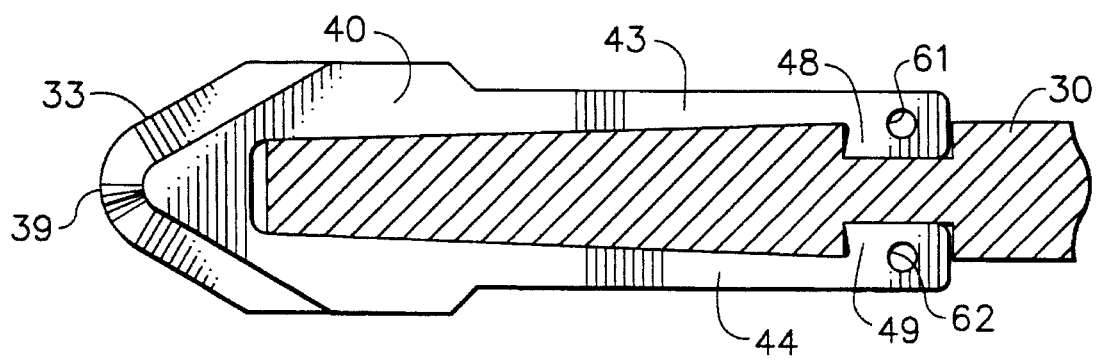
FIG. 13 is a side elevational view illustrating the attachment of the alternative piercing tip illustrated in FIGS. 8, 11 and 12 to the obturator stem of the trocar.

FIGS. 8 and 11–13 illustrate an alternative embodiment for the piercing tip of the obturator. Component parts which are identical to those of the previous embodiment have been numbered the same for ease of reference. In this embodiment, the first and second legs are integral with and extend away from the first and second base portions of the piercing tip. FIG. 13 nicely illustrates the tapering of the first and second slots from the deep region adjacent the cutting edge surface to the shallow region adjacent the first and second notches.

In another embodiment of this invention which is not specifically illustrated in the drawings, the distal end of the obturator assembly can be rotatably attached to the remainder of the assembly using conventional attachment methods. If the piercing tip is inadvertently rotated during penetration, the distal end of the obturator assembly, including the safety shield, will correspondingly rotate. This rotation feature may reduce undesirable tissue trauma caused by unwanted rotation of the piercing tip.

While this invention has been described in connection with its most preferred embodiment, numerous additional embodiments will be readily apparent to those skilled in the art. For example, and not by way of limitation, the piercing tip may be conical or perimetal instead of flat. The scope of the invention is defined by the claims which appear below, and this specification is not intended to limit the scope of the claimed invention.

What is claimed is:

1. A surgical trocar comprising an obturator, said obturator having:

a) an obturator housing at a first end of said obturator;

b) a piercing tip at an opposite end of said obturator for piercing bodily tissue, said piercing tip including a cutting edge surface and first and second spaced-apart legs generally parallel to each other extending away from said cutting edge surface, said first and second legs having first and second inwardly-extending, mutually opposed barbs thereon; and c) an elongated rigid stem having a distal tip thereon, said stem attached to said obturator housing at said first end of said obturator, said stem having first and second sidewalls thereon, said sidewalls having first and second slots disposed therein and first and second notches embedded therein, said first and second legs of said piercing tip being straddled about said stem at said opposite end of said obturator, said first and second legs being disposed within said first and second slots embedded in said sidewalls of said stem, and said first and second barbs of said legs being embedded in said first and second notches of said stem so as to attach said piercing tip to said stem; wherein said first and second slots are tapered from a deep region adjacent said distal tip of said stem to a shallow region adjacent said first and second notches.

2. The trocar of claim 1 wherein said piercing tip has first and second planar surfaces generally parallel to each other, said surfaces converging to said cutting edge surface of said piercing tip.

3. The trocar of claim 2 wherein said stem has a distal tip, and said distal tip has a tip slot interposed between said first and second slots.

4. The trocar of claim 3 wherein said planar surfaces of said piercing tip are embedded in said tip slot.

5. The trocar of claim 4 wherein said distal tip of said stem is rounded.

6. The trocar of claim 5 wherein said tip slot merges with said first and second slots so as to form a continuous attachment slot for said piercing tip.

7. A surgical trocar comprising an obturator, said obturator having:

a) an obturator housing at a first end of said obturator;

b) a piercing tip at an opposite end of said obturator for piercing bodily tissue, said piercing tip including (i) first and second planar surfaces generally parallel to each other, said planar surfaces extending in a distal direction from a base and converging to a cutting edge surface of said piercing tip remote from said base, (ii) first and second spaced-apart legs generally parallel to each other extending in a proximal direction from said base and away from said cutting edge surface, (iii) first and second elongated base portions extending from said base of said planar surfaces in said proximal direction, and (iv) first and second longitudinal piercing tip slots separating said first and second elongated base portions from said first and second legs; and c) an elongated rigid stem, said stem attached to said obturator housing at said first end of said obturator, and said first and second legs of said piercing tip being straddled about said stem at said opposite end of said obturator so as to attach said piercing tip to said stem.

8. The trocar of claim 7 wherein said stem has first and second sidewalls, and said first and second legs are disposed within first and second stem slots embedded in said sidewalls of said stem.

9. The trocar of claim 8 wherein said first and second legs have first and second inwardly-extending, mutually opposed barbs.

10. The trocar of claim 9 wherein said stem has first and second notches disposed in said first and second sidewalls of said stem, and said first and second barbs of said legs are embedded in said first and second notches.

11. The trocar of claim 10 wherein said stem has a distal tip thereon, and said distal tip has a tip slot interposed between said first and second stem slots.

12. The trocar of claim 11 wherein said planar surfaces of said piercing tip are embedded in said tip slot.

13. The trocar of claim 12 wherein said distal tip of said stem is rounded.

14. The trocar of claim 13 wherein said tip slot merges with said first and second slots so as to form a continuous attachment slot for said piercing tip.

15. The trocar of claim 14 wherein said first and second stem slots are tapered from a deep region adjacent said tip slot to a shallow region adjacent said first and second notches.

* * * * *